US006484052B1

United States Patent
Visuri et al.

(10) Patent No.: US 6,484,052 B1
(45) Date of Patent: Nov. 19, 2002

(54) OPTICALLY GENERATED ULTRASOUND FOR ENHANCED DRUG DELIVERY

(75) Inventors: Steven R. Visuri, Livermore, CA (US); Heather L. Campbell, Baltimore, MD (US); Luiz Da Silva, Danville, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/281,371

(22) Filed: Mar. 30, 1999

(51) Int. Cl.$^7$ ............................................... A61N 1/30
(52) U.S. Cl. ......................................... 604/20; 606/15
(58) Field of Search ....................... 604/20–22; 606/7, 606/15, 16, 9; 607/88, 89

(56) References Cited

U.S. PATENT DOCUMENTS

| 5,836,940 | A | * | 11/1998 | Gregory | ...................... | 606/15 |
| 6,022,309 | A | * | 2/2000 | Celliers et al. | ................ | 600/7 |
| 6,135,976 | A | * | 10/2000 | Tachibana et al. | ............ | 604/21 |

* cited by examiner

Primary Examiner—Manuel Mendez
(74) Attorney, Agent, or Firm—John P. Wooldrige; Alan H. Thompson

(57) ABSTRACT

High frequency acoustic waves, analogous to ultrasound, can enhance the delivery of therapeutic compounds into cells. The compounds delivered may be chemotherapeutic drugs, antibiotics, photodynamic drugs or gene therapies. The therapeutic compounds are administered systemically, or preferably locally to the targeted site. Local delivery can be accomplished through a needle, cannula, or through a variety of vascular catheters, depending on the location of routes of access. To enhance the systemic or local delivery of the therapeutic compounds, high frequency acoustic waves are generated locally near the target site, and preferably near the site of compound administration. The acoustic waves are produced via laser radiation interaction with an absorbing media and can be produced via thermoelastic expansion, thermodynamic vaporization, material ablation, or plasma formation. Acoustic waves have the effect of temporarily permeabilizing the membranes of local cells, increasing the diffusion of the therapeutic compound into the cells, allowing for decreased total body dosages, decreased side effects, and enabling new therapies.

87 Claims, 2 Drawing Sheets

US 6,484,052 B1

OPTICALLY GENERATED ULTRASOUND FOR ENHANCED DRUG DELIVERY

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to techniques for drug delivery, and more specifically, it relates to the use of acoustic waves for the enhancement of drug delivery.

2. Description of Related Art

Ultrasound-enhanced drug delivery has been postulated to work through a variety of mechanisms. Most notably, ultrasound produces cavitation bubbles, which are thought to disrupt the lipid bilayer membrane of cells (Mitragotri, et al. Pharm Res 1996; 13: 411–420). This disruption can cause channels to form, which can temporarily increase a cell's permeability to certain drug compounds. The concentration of compounds which normally have low diffusion rates into the cell can be increased. Transdermally (across the skin), it has been shown that the permeability of disordered lipid bilayers can be up to 5000-fold higher than the diffusion coefficients in normal lipid bilayers (Mitragotri 1996). Other compounds, to which the cell is usually impermeable, can also be driven into the cell through the use of ultrasound.

Extracorporeal (transdermal) application of ultrasound is inappropriate when deeper penetration of the ultrasound is required for enhanced drug delivery in remote locations. In the current transdermal method, the drug of interest is applied to the skin and ultrasound is generated through the placement of a piezoelectric transducer on the skin. This ultrasound could be focused into deeper structures, similar to ultrasound imaging transducers. However, it is difficult to assess or control dosimetry to deeper structures with this method and the ultrasound does not penetrate through gas filled organs or high density tissues such as bone. If one transducer is used, a high amount of power is necessary to generate the required ultrasound in the underlying tissues. The high power needed can cause thermal damage to the skin. An array of transducers could be used to focus onto a single point beneath the skin. However, the amount of heat and stress produced as the ultrasound waves converge, may produce damage to the underlying tissue, including those that are not intended to be treated. Local generation of ultrasound solves many of these potential problems. However, the use of traditional piezoelectric materials such as PZT induce other complications. These materials need electrical stimulation, which is undesirable to deliver inside the body. Further, the large size of the piezoelectric materials required to achieve necessary ultrasound magnitudes, forbids certain in vivo applications. The present invention, with its local generation and delivery of optically generated ultrasound, facilitates the delivery of ultrasound at required intensities into remote locations.

U.S. Pat. No. 4,767,402, issued Aug. 30, 1988, titled "Ultrasound Enhancement Of Transdermal Drug Delivery" is directed to a method using ultrasound for enhancing and controlling transdermal permeation of a molecule, including drugs, antigens, vitamins, inorganic and organic compounds, and various combinations of these substances, through the skin and into the circulatory system. The frequency and intensity of ultrasonic energy which is applied, the media between the ultrasonic applicator and the skin, and the length of time of exposure are determined according to the type of skin and the substance to be diffused transdermally. Levels of the diffused molecules in the blood and urine measured over a period of time are initially used to determine under what conditions adequate transfer occurs. In general, the frequency range of the ultrasound is between 20 kHz and 10 MHz, with intensities between 0 and 3 W/cm$^2$. Intensity is decreased as the frequency is decreased to prevent damage to the skin. The preferred range of frequencies is between 0.5 MHz and 1.5 MHz and the preferred range of intensities is between 2 and 4 W/cm$^2$. Exposure is for between 1 and 10 minutes for most medical uses. The ultrasound may be pulsed or continuous. However, the frequency, intensity and time of exposure are interdependent as well as a function of the molecule being diffused and the nature of the skin at the site of exposure. One way of determining the maximum limit of exposure is to measure skin temperature, decreasing or stopping the treatment when the temperature of the skin rises one to two degrees Centigrade.

In U.S. Pat. No. 5,386,837, issued Feb. 7, 1995, titled "Method For Enhancing Delivery Of Chemotherapy Employing High-Frequency Force Fields" pulse shocks of high-frequency wave energy (e.g. RF, microwave, high-energy infra-red or laser electromagnetic wave energy or ultrasonic acoustic wave energy), rather than DC electric pulses, are employed to non-invasively produce, with minimal or, if desired, a controlled amount of temperature rise in a patient's body tissues, force fields of an intensity sufficient to create transient pores in the plasma membranes of targeted cells, such as tumor or other diseased cells, through which chemotherapeutic agents can easily be delivered, enter and taken up by these targeted cells, even for (1) deep-seated cells (e.g., the cells of a deep-seated tumor) or (2) non-localized diseased cells (e.g., metastasized tumor cells) within a patient's body.

U.S. Pat. No. 5,421,816, issued Jun. 6, 1995, titled "Ultrasonic Transdermal Drug Delivery System" described the use of Ultrasonic energy to release a stored drug and forcibly move the drug through the skin of an organism into the blood stream. A housing (81) includes a cavity (67) defined by an assembly of ultrasonic transducers (65) and separated from the skin by a polymeric membrane (69) that stores the drug to be delivered. The ultrasonic transducer assembly includes a flat, circular ultrasonic transducer (85) that defines the top of a truncated cone and a plurality of transducer segments (87a, 87b, 87c, 87d . . . ) that define the walls of the cone. The resonant frequency of the planar transducer is lower than the resonant frequency of the transducer segments. The planar, flat, circular transducer generates fixed frequency (5 KHz–1 MHz range) ultrasonic stimuli impulses for a predetermined period of time (10–20 seconds). Between the stimuli pulse periods, the transducer segments receive variable frequency ultrasonic pumping pulses. Preferably, the variable frequency ultrasonic pumping pulses lie in the 50 MHz–300 MHz range. The variable frequency ultrasonic pumping pulses are applied to opposed transducer segments. The transducer segments create beams that impinge on the skin at an oblique angle and create a pulsating wave. Further, the variable frequency ultrasonic pumping pulses are applied to opposing transducer segments in a rotating manner to create pulsating waves in the skin in a variety of directions. The stimuli pulses cause the planar transducer to produce an ultrasonic wave that excites the local nerves in the way that trauma (heat, force) excites the local nerves. The nerve excitation opens the epidermal/ dermal junction membrane and the capillary endothelial cell joints. The variable frequency ultrasonic pumping pulses cause the transducer segments to produce ultrasonic waves in both the polymeric membrane and the skin. The ultrasonic waves pump the drug first through the polymeric membrane and then through, skin openings into the underlying blood vessels. The control electronics apply ultrasonic stimuli pulses to the skin by energizing the stimuli transducer at a first frequency, preferably lying in the 5 KHz–1 MHz range for a predetermined period of time (10–20 seconds). Between the stimuli pulse periods, the control electronics apply variable frequency ultrasonic pumping pulses to the skin by energizing the pumping transducer segments. Preferably, the frequency of the variable frequency ultrasonic pumping pulses lie in the 50 MHz–300 MHz range U.S. Pat. No. 5,445,611, issued Aug. 29, 1995, titled "Enhancement Of Transdermal Delivery With Ultrasound And Chemical Enhancers" discloses a method of enhancing the permeability of the skin or mucosa to a biologically active permeant or drug is described utilizing ultrasound or ultrasound plus a chemical enhancer. If desired the ultrasound may be modulated by means of frequency modulation, amplitude modulation, phase modulation and/or combinations thereof. A frequency modulation from high to low develops a local pressure gradient directed into the body, thus permitting permeant to traverse the skin or mucosa. The enhanced delivery is preferably accomplished using a chemical enhancer, applying ultrasound optionally at a modulated frequency, amplitude, phase, or combinations thereof that further induces a local pressure gradient into the body. The method is also useful as a means for application of a tattoo by noninvasively delivering a pigment through the skin surface.

U.S. Pat. No. 5,614,502, issued Mar. 25, 1997, titled "High Pressure Impulse Transient Drug Delivery for the Treatment of Proliferative Diseases" described the use of high pressure shock waves in combination with sub-toxic doses of compounds to treat proliferative diseases. A related patent, U.S. Pat. No. 5,658,892, issued Aug. 19, 1997, titled "Compound Delivery Using High-Pressure Impulse Transients" discussed a method for increasing the delivery of a compound to the interior of a cell using a time-dependent pressure impulse. These two patents describe a technique that is intended to deliver a low number (typically less than 20) of fast rise-time (typically less than 35 ns), high pressure magnitude (typically 250–350 bars) acoustic waves to a collection of biological cells. Simultaneous administration of a therapeutic compound and the acoustic wave(s), enhance the delivery of the compound compared to normal passive diffusion. Means are discussed for creation of the acoustic shock waves and for selection of compound dosages based on the therapeutic index.

SUMMARY OF THE INVENTION

The invention is a means of locally producing high frequency acoustic waves, analogous to ultrasound, in vivo for the purpose of enhancing the delivery of therapeutic compounds into cells. This technique involves treating diseased or hyper-proliferative cells, such as those responsible for vascular hyperplasia leading to restenosis, and carcinomas, neoplasms, and sarcomas. The compounds delivered may be chemotherapeutic drugs (such as Taxol, 5-Aminoaleuvenic acid, anthracyclines), antibiotics, photodynamic drugs (such as psoralans, porphyrin derivatives), or gene therapies (RNA, DNA).

The therapeutic compounds are administered systemically, or preferably locally to the targeted site. Local delivery can be accomplished through a needle, cannula, or through a variety of vascular catheters, depending on the location of routes of access. Natural barriers may be used to limit diffusion of the compounds, or mechanical barriers such as a balloon catheter to dam a drug within a blood vessel.

To enhance the systemic or local delivery of the therapeutic compounds, high frequency acoustic waves are simultaneously delivered. The acoustic waves are generated locally near the target site, and preferably near the site of compound administration. The acoustic waves are produced via laser radiation interaction with an absorbing media and can be produced via thermoelastic expansion, thermodynamic vaporization, material ablation, or plasma formation. Ideally, a thermoelastic or thermodynamic mechanism is employed. For example, as a short burst of laser radiation is deposited into a strongly absorbing material, the material rapidly heats and expands, sending an acoustic wave into the surrounding media. The laser radiation may be delivered to a remote location via a fiber optic passed through a catheter or other cannula. Absorption of laser radiation may take place in native tissues or fluids, in applied absorbing dyes, in the therapeutic compound, or in a transducer placed near the target sight. An ultrasound effect may be produced by the delivery of laser pulses at high frequencies, greater than 100 Hz, and preferably greater than 1000 Hz. This ultrasound has the effect of temporarily, but non-toxically permeabilizing the membranes of local cells, increasing the diffusion of the therapeutic compound into the cells. In this way, the effectiveness of the compounds may be increased, allowing for decreased total body dosages, decreased side effects, and enabling new therapies.

DETAILED DESCRIPTION OF THE INVENTION

This invention provides optical generation of acoustic waves for enhancement of drug delivery into cells. The invention involves producing a range of acoustic wave frequencies (100 Hz–1 MHz) and a range of pressure intensities (0.1 bar to 100 bar), below the thermal and mechanical threshold for massive cell damage. This invention may be catheter-based in which optical energy is delivered through an optical fiber and deposited in an absorbing fluid or solid at the end of the catheter. This deposited energy creates an acoustic impulse in the absorber through thermoelastic and/or thermodynamic mechanisms. A catheter-based system describing the thermoelastic and/or thermodynamic mechanisms of the present invention is disclosed in U.S. patent application Ser. No. 08/639017, titled "Opto-Acoustic Thrombolysis" which disclosure is incorporated herein by reference. Thus, an acoustic field is established locally. This could be applied in vivo (intravascularly, intraluminally or otherwise percutaneously) or transdermally for drug delivery enhancement into tissues and cells.

Figure 1A:
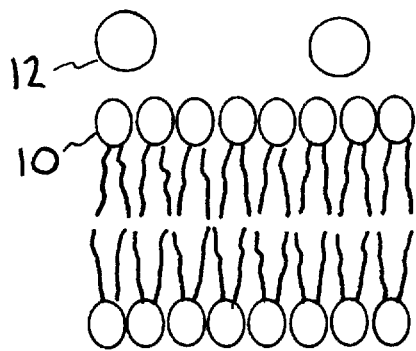
FIG. 1A shows a conceptual view of a normal lipid bilayer.
Figure 1B:
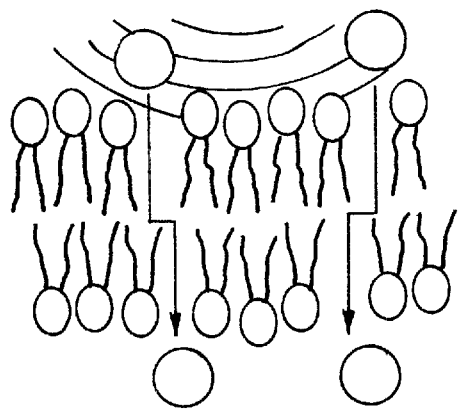
FIG. 1B depicts the case where ultrasound has transiently disordered the cell membrane to allow passage of the drug molecule through the lipid bilayer.

As briefly described above, ultrasound can produce cavitation bubbles, which are postulated to disrupt the lipid bilayer membrane of cells. This disruption can cause temporary channels to form in the cell membrane. FIG. 1A shows a conceptual view of a normal lipid bilayer. Tight junctions of the bilayer prevent drug molecules 12 from passing through the lipid bilayer. FIG. 1B depicts the case where ultrasound has transiently disordered the cell membrane to allow passage of the drug molecule through the lipid bilayer. This temporary disruption of a cell's barrier can increase intracellular concentrations of compounds which normally are impermeable or have low diffusion rates.

An optical fiber guides the laser energy through the catheter. The use of optical fibers offers a number of advantages. Optical fibers can be fabricated to small dimensions, are highly transparent and are capable of delivering substantial optical power densities from the source to the delivery site with little or no attenuation.

Figure 2:
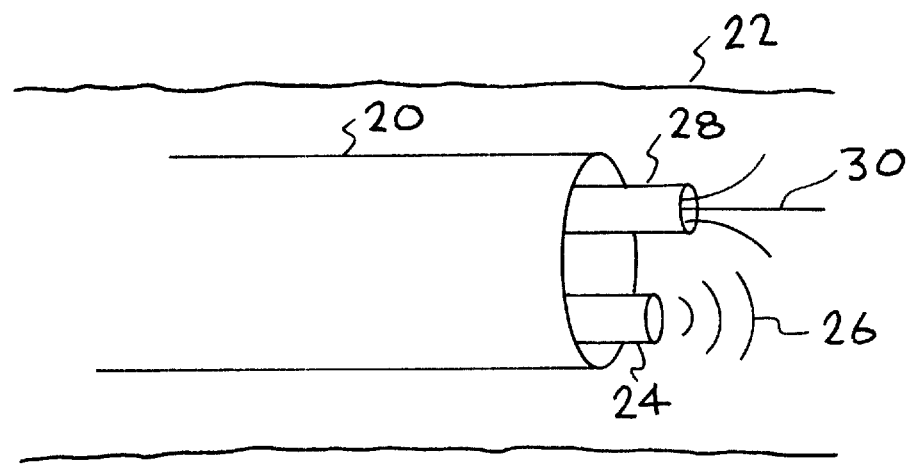
FIG. 2 shows the distal end of a catheter-based or introducer needle system for ultrasound enhanced drug delivery.

The fiber is coupled to a laser system. The laser light that emerges from the fiber is absorbed either by native fluids, such as blood, or by an exogenous absorber, such as a biological saline solution containing an absorbing dye, or a solid absorber such as a plastic or metal. The optical energy that is transmitted through the optical fiber creates an acoustic field in the absorbing fluid, through thermoelastic and/or thermodynamic mechanisms. The subsequent acoustic energy acts as a drug delivery enhancer. FIG. 2 shows the distal end of a catheter-based or introducer needle system for ultrasound enhanced drug delivery. A catheter or introducer needle 20 is located within an artery wall 22. The catheter includes at least one optical fiber 24 for providing laser light to generate an acoustic radiation field, as depicted by reference numeral 26. The catheter 20 includes at least one working channel 28, which provides delivery of a drug, as depicted by reference numeral 30.

The thermoelastic mechanism involves the expansion and contraction of the absorbing material. When the optical energy is deposited into the absorber as heat, a region of high pressure is created. This high pressure zone decays into two waves: a compression wave propagates away from the energy deposition region and a rarefaction wave converges on the center of the energy deposition region. When the rarefaction wave converges on the center of the initial deposition region, it can create a region of tensile stress that may promote the formation of a cavitation bubble. Eventually, with the decay of the tensile stress, the cavity collapses. Collapse and subsequent rebound of the cavitation bubble will generate acoustic impulses in the surrounding fluid, which will carry off a portion of the energy of the cavity. The first collapse and rebound will be followed by subsequent collapse and rebound events of diminishing intensity until the energy of the cavity is dissipated in the fluid. Subsequent laser pulses are delivered to repeat or continue this cycle of compressive and tensile acoustic waves and generate a local ultrasonic radiation field. The acoustic waves can be formed by electrical stimulation of piezoelectric material, discharge of an electrical current across a spark gap, or preferably delivery of pulses of electromagnetic energy from a laser into an absorber. The laser mechanisms of acoustic wave formation may utilize plasma formation, material ablation, or preferably thermoelastic expansion of thermodynamic vaporization. The laser parameters for thermoelastic expansion include: (i) a pulse frequency within the range of 100 Hz to 1 MHz, (ii) a wavelength within the range of 200 nm to 5000 nm, (iii) pulse duration of 1 fs to 1 ms, and (iv) a fluence within the range of 0.01 J/cm$^2$ to 25 J/cm$^2$.

The thermodynamic mechanism involves the formation and collapse of vapor bubbles in the absorbing fluid. The optical energy which is delivered into the fluid causes the superheating of the fluid. This superheating causes an explosive vaporization process, which creates a bubble of vapor. In the process of expanding, the bubble launches an acoustic wave in the fluid, which propagates out from the heated region. The bubble expands until the vapor pressure is less than the ambient pressure, at which point, the bubble undergoes collapse. The bubble expansion and collapse couples acoustic energy into the fluid. Subsequent laser pulses are delivered to continue this cycle and generate a local ultrasonic radiation field.

Figure 3A:
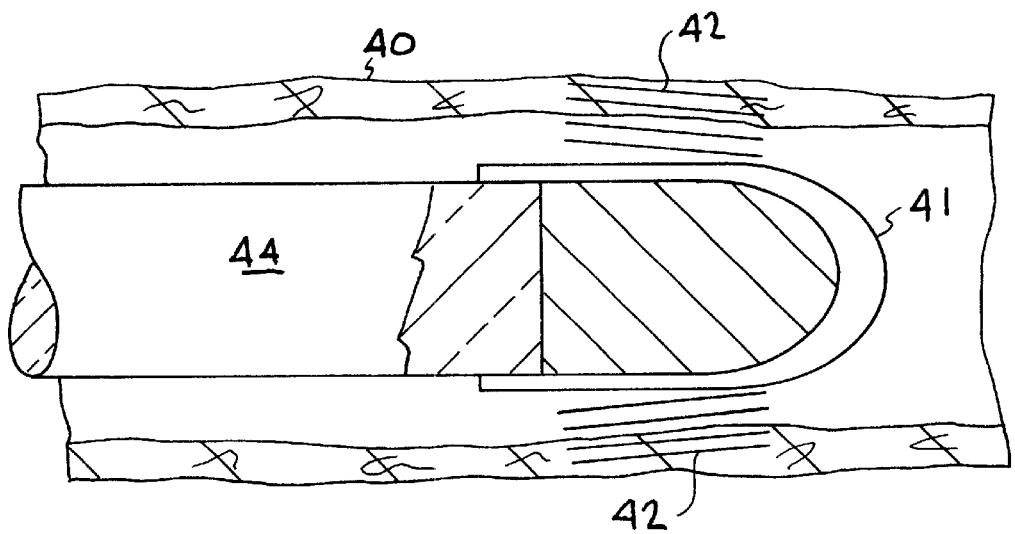
FIGS. 3A–C show designs of transducers to direct the acoustic wave radially for use in cylindrical or spherical applications.
Figure 3B:
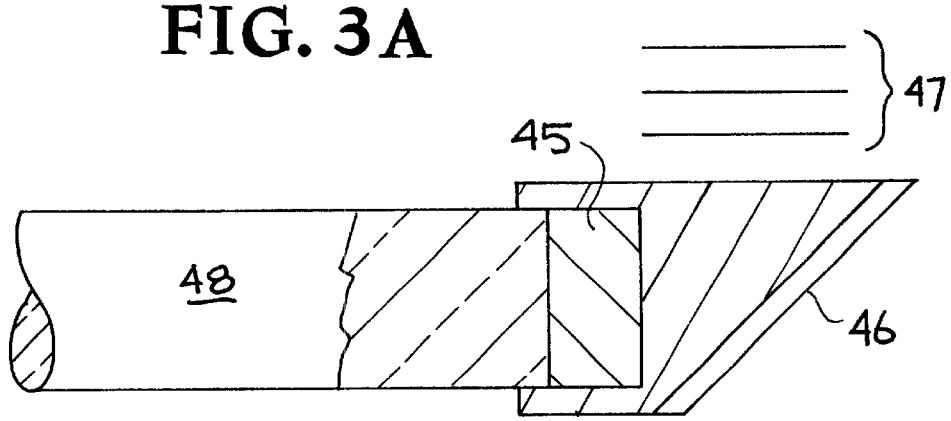
Figure 3C:
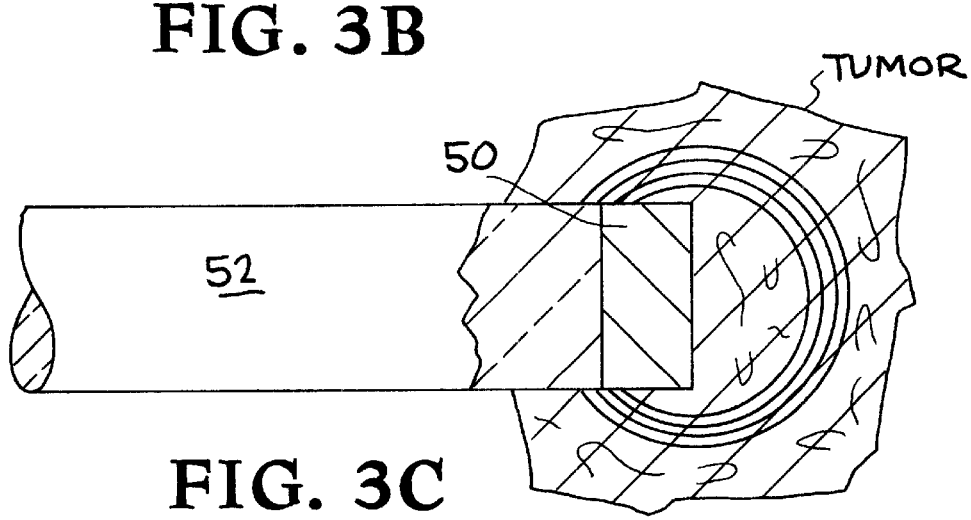

These mechanisms may be produced by interaction with native or exogenous absorbers. Strong absorption and shallow penetration into the absorber is generally required. Therefore, specific laser wavelengths may be chosen for efficient and potentially selective absorption. A variety of transducer tips designs may be implemented, constructed of plastics/polymers, metals, and others. These tips may be affixed to the end of the optical fiber and be simple in geometry, for example cylindrical, or more complex to focus or direct the emitted acoustic wave. FIGS. 3A–C show designs of transducers to direct the acoustic wave radially for use in cylindrical or spherical applications. For example, to address the walls of an artery 40, FIG. 3A shows an elongated transducer 41 with less absorption (longer penetration depth) for directing acoustic waves 42 perpendicular to the optical fiber 44 axis. As shown in FIG. 3B, a transducer 45 could have an angled reflective material 46 at the tip, such that a forward propagating acoustic wave would be reflected, at an angle near 90 degrees, towards the perpendicular. The figure shows a fiber 48 with an angled reflective material 46 and an acoustic wave 47 reflected, at an angle near 90 degrees. The sperical shaped transducer 50 connected to the end of a fiber optic 52, as shown in FIG. 3C, will produce a spherical wave. Transducer materials should be chosen to best match acoustic impedance of the surrounding material for optimal transmission of acoustic energy. Alternatively, large impedance mismatches are used to reflect greater amounts of energy. To cover broad areas, within a lumen or organ, multiple transducers may be required. Small diameter optical fibers may be implemented to enable flexibility and limit size of a multi-fiber device. The array of transducers may be arranged along the catheter axis, or in any appropriate 3-dimensional configuration.

The operation of these devices inherently involves waste heat production at the tip. Although heat often stimulates circulation and speeds chemical interaction, excessive heat should generally be mitigated. Limiting the thermal load of the transducer tips, where required, can be achieved by duty cycling the acoustic wave source. Alternatively, a convective cooling system can be employed in which air or fluid flows over or through the transducer. If the acoustic source is laser generated thermoelastic expansion, and the absorbing media is a fluid, then the absorbing fluid could also act as the cooling agent. The coolant can be pumped from a proximal position (outside the patient) through the catheter, to the transducer tip, and return to the reservoir pump.

Another mechanism by which the ultrasound could be produced is through an optically-powered, mechanical transducer. The transducer would be filled with an absorbing dye. The transducer would be placed on the distal end of the optical fiber, within a catheter. One type of transducer is cylinder-shaped, in which the distal end acts as a diaphragm, expanding and contracting with the formation and collapse of the bubbles within the absorbing fluid. Another type of transducer is bellows-shaped. The formation and collapse of the bubbles within the absorbing fluid causes the expansion and contraction of the entire transducer, in a manner similar to an accordion. Transducers usable in the present invention are described in U.S. patent application Ser. No. 08/639018, titled "Opto-Acoustic Transducer For Medical Applications" which disclosure is incorporated herein by reference. An option for localized drug delivery in this method is to use a transducer with pores. The drug would be driven out of the transducer with the increased pressure caused by the cavitation and/or vapor bubbles.

This technique may also incorporate a feedback mechanism for monitoring and controlling the magnitude of the acoustic vibrations induced in the surrounding fluids and tissues. This feedback system may be constructed of piezoelectric materials in which an electrical signal is generated proportional to the compression or tension of the material. Alternatively, the feedback system may incorporate optical diagnostics such as a Fabry-Perot interferometer. This interferometer can be constructed by mounting a thin film at the distal fiber tip and illuminating with a continuous wave (cw) laser. As an acoustic wave alters the optical pathlength of the film, the phase of the cw-laser reflections from the two surfaces of the film is changed. This is evident as a change in the amplitude of the return signal that can be detected with a photodetector.

Another embodiment of the present invention increases the efficiency of previous devices through the use of an echo-contrast agent. These agents contain or initiate the formation of microbubbles. These agents are typically used to increase the contrast of ultrasound imaging by increasing the reflected signal in the area of the contrast agent. In the presence of ultrasound fields, these microbubbles also increase the likeliness of producing cavitation. Since cavitation is likely the primary mechanism of ultrasound enhanced drug delivery, echo contrast agents can increase the efficiency of cavitation production and cell permeation. To this end, echo contrast is delivered to the site of the ultrasound production via a catheter or needle prior to or during ultrasound application. The presence of microbubbles in the contrast agent.provide an initiation site for cavitation, increasing the likeliness of cavitation or decreasing the required tensile pressures. Therefore, ultrasound pressure magnitudes can be lower and consequently optical energy can be decreased. The echo-contrast agent can contain the therapeutic drug or microbubbles may be formed in the drug to act as the 'contrast agent'. Typical contrast agents consist of albumin-stabilized microbubbles, stabilized sulfur hexafluoride, galactose/palmitic acid, or other means of creating or entrapping gas bubbles of 0.1–100 µm diameter. Typically these bubbles are in the range of 1–4 µm in diameter.

Changes and modifications in the specifically described embodiments can be carried out without departing from the scope of the invention, which is intended to be limited by the scope of the appended claims.

The invention claim is:

1. A method for enhancing drug delivery, comprising:
   inserting a fiber optic to a drug delivery point within a medium, wherein said fiber optic comprises a proximal end and a distal end, wherein said medium is selected from a group consisting of a portion of a human body and a portion of an animal body;
   delivering a drug to said drug delivery point; and
   coupling laser light into said proximal end, wherein said laser light has (i) a pulse frequency within the range of 100 Hz to 1 MHz, (ii) a wavelength within the range of 200 nm to 5000 nm, (iii) a pulse duration within the range of 1 fs to 1 ms and (iv) a-fluence within the range of 0.01 J/cm$^2$ to 25 J/cm$^2$, wherein said laser light emerges from said distal end and generates an acoustic radiation field within said medium, wherein said acoustic radiation field is generated through one or more mechanisms selected from a group consisting of thermoelastic expansion within said medium and superheated vapor expansion within said medium, wherein said acoustic radiation field enhances drug delivery to surrounding cells.

2. A method for enhancing drug delivery, comprising:
   inserting a fiber optic to a drug delivery site within a medium, wherein said fiber optic comprises a proximal end and a distal end, wherein said medium is selected from a group consisting of a portion of a hum an body and a portion of an animal body; and
   delivering a drug to said drug delivery site; and
   generating an acoustic radiation field with said medium near said drug delivery site by coupling laser light into said proximal end of said fiber optic, wherein said acoustic radiation field enhances drug delivery to surrounding cells.

3. The method of claim 2, wherein said acoustic radiation field is generated through at least one mechanism selected from a group consisting of thermoelastic expansion within said medium and superheated vapor expansion within said medium.

4. The method of claim 3, wherein said laser light has (i) a pulse frequency within the range of 100 Hz to 1 MHz, (ii) a wavelength within the range of 200 nm to 5000 nm, (iii) a pulse duration within the range of 1 fs to 1 ms and (iii) a-fluence within the range of 0.01 J/cm$^2$ to 25 J/cm$^2$.

5. The method of claim 2, wherein said drugs are selected from a group consisting of chemotherapeutic drugs, antibiotics, photodynamic drugs, and gene therapies.

6. The method of claim 5, wherein said chemotherapeutic drugs are selected from a group consisting of Taxol, 5-Aminoaleuvenic acid and anthracyclines.

7. The method of claim 5, wherein said photodynamic drugs are selected from a group consisting of psoralans and porphyrin derivatives.

8. The method of claim 5, wherein said gene therapies are selected from a group consisting of RNA therapies and DNA therapies.

9. The method of claim 2, wherein the step of delivering a drug to said drug delivery site includes administering therapeutic compounds systemically.

10. The method of claim 2, wherein the step of delivering a drug to said drug delivery site includes administering therapeutic compounds locally to said drug delivery site.

11. The method of claim 10, wherein the step of administering therapeutic compounds locally to said drug delivery site is accomplished by delivering a drug through a delivery mechanism selected from a group consisting of a needle, a cannula and a vascular catheter.

12. The method of claim 10, wherein the step of administering therapeutic compounds locally to said drug delivery site includes utilizing natural barriers within the vasculature to limit diffusion of said compounds.

13. The method of claim 10, wherein the step of administering therapeutic compounds locally to said drug delivery site includes utilizing mechanical barriers to limit diffusion of said compounds.

14. The method of claim 13, wherein said mechanical barriers comprise a balloon catheter to dam said drug within a blood vessel.

15. The method of claim 2, wherein said acoustic radiation field is generated through at least one mechanism selected from a group consisting of material ablation and plasma formation.

16. The method of claim 2, wherein said acoustic radiation field is generated by absorption of laser radiation in at least one medium selected from a group consisting of native tissues, native fluids, applied absorbing dyes and a therapeutic compound.

17. The method of claim 2, wherein said acoustic radiation field temporarily, but non-toxically permeabilizes the membranes of local cells, increasing the diffusion of a therapeutic compound into said cells.

18. The method of claim 2, wherein said acoustic radiation field comprises a pressure within the range of 0.1 bar to 100 bar.

19. The method of claim 2, wherein said fiber optic is located within a catheter.

20. The method of claim 19, wherein said drug is delivered through a working channel located within said catheter.

21. The method of claim 2, wherein the step of generating an acoustic radiation field acts as a drug delivery enhancer by disrupting the lipid bilayer membrane of cells near said drug delivery site to cause temporary channels to form in the membrane of said cells, wherein said acoustic radiation field transiently disorders said membrane to allow passage of drug molecules through said lipid bilayer, wherein the temporary disruption of a said membrane increases intracellular concentrations or diffusion rates of compounds.

22. The method of claim 2, wherein said fiber optic is coupled to a laser system.

23. The method of claim 2, wherein said laser light that emerges from said distal end of said fiber optic is absorbed by at least one medium selected from a group consisting of native fluids, such as blood, an exogenous absorber, such as a biological saline solution containing an absorbing dye, and a solid absorber such as a plastic or metal.

24. The method of claim 23, wherein said native fluids comprise blood.

25. The method of claim 23, wherein said exogenous absorber comprises a biological saline solution containing an absorbing dye.

26. The method of claim 23, wherein said solid absorber is selected from a group consisting of plastic and metal.

27. The method of claim 2, wherein the step of generating an acoustic radiation field includes producing acoustic waves by a method selected from a group consisting of electrically stimulating piezoelectric material, discharging an electrical current across a spark gap and delivering pulses of electromagnetic energy from a laser into an absorber.

28. The method of claim 4, wherein the step of generating an acoustic radiation includes producing acoustic waves by a method selected from a group consisting of plasma formation, material ablation, thermoelastic expansion and thermodynamic vaporization.

29. The method of claim 4, wherein the step of generating an acoustic radiation field is accomplished by delivering said laser light to a transducer tip affixed to said distal end of said fiber optic.

30. The method of claim 29, wherein said transducer comprises material selected to match the acoustic impedance of said ambient medium for optimal transmission of acoustic energy.

31. The method of claim 29, wherein said transducer comprises material selected to produce large impedance mismatches to reflect greater amounts of energy.

32. The method of claim 4, wherein the step of generating an acoustic radiation field is accomplished by delivering said laser light through a plurality of fiber optics, wherein each fiber optic of said plurality of fiber optics comprises a distal end, wherein a transducer tip is affixed to each distal end to cover broad areas, within a lumen or organ.

33. The method of claim 29, wherein waste heat produced at said distal end is mitigated by duty cycling said laser light.

34. The method of claim 29, wherein waste heat produced at said distal end is mitigated by a convective cooling system in which air or fluid flows over or through said transducer.

35. The method of claim 29, wherein coolant is pumped from a proximal position through said catheter, to said transducer tip and returned to a reservoir pump.

36. The method of claim 4, wherein an absorbing fluid filled optically-powered mechanical transducer is attached to said distal end of said fiber optic.

37. The method of claim 36, wherein said absorbing dye filled optically-powered mechanical transducer is a cylinder-shaped diaphragm which expands and contracts with the formation and collapse of bubbles within said absorbing dye.

38. The method of claim 36, wherein said absorbing dye filled optically-powered mechanical transducer comprises a bellows.

39. The method of claim 4, wherein said drug is located within an optically-powered mechanical transducer which comprises pores, wherein said drug is driven out of said transducer with the increased pressure caused by bubbles produced by said laser light.

40. The method of claim 2, further comprising monitoring and controlling the magnitude of said acoustic radiation field with a feedback system.

41. The method of claim 40, wherein said feedback system comprises piezoelectric materials in which an electrical signal is generated proportional to said acoustic radiation field.

42. The method of claim 2, further comprising illuminating with a continuous wave laser a thin film mounted on said distal end of said fiber optic to produce laser reflections having an amplitude, wherein said thin film comprises an optical pathlength, wherein said acoustic radiation field alters said optical pathlength thereby altering said amplitude of said laser reflections, wherein said method further comprises monitoring said amplitude with a photodetector.

43. The method of claim 29, further comprising monitoring the reflections of two surfaces of a thin film mounted at the end of said transducer.

44. The method of claim 2, further comprising delivering an echo contrast agent near said drug delivery site, wherein said echo contrast agent further enhances the absorption of said drug.

45. The method of claim 44, wherein said echo contrast agent is delivered to said drug delivery site prior the step of generating said acoustic radiation field.

46. The method of claim 44, wherein said echo contrast agent is delivered to said drug delivery site during the step of generating said acoustic radiation filed.

47. The method of claim 19, further comprising delivering an echo contrast agent near said drug delivery site, wherein said echo contrast agent further enhances the absorption of said drug, wherein said echo contrast agent is delivered through a working channel located within said catheter.

48. The method of claim 19, further comprising delivering an echo contrast agent near said drug delivery site, wherein said echo contrast agent further enhances the absorption of said drug, wherein said echo contrast agent is delivered through a needle.

49. The method of claim 44, wherein said echo contrast agent is selected from a group consisting of albumin-stabilized microbubbles, stabilized sulfur hexafluoride and galactose/palmitic acid.

50. The method of claim 44, wherein said echo contrast agent comprises gas bubbles having a diameter within the range of 0.1–100 µm.

51. An apparatus for enhancing drug delivery, comprising:
a fiber optic for insertion into to a drug delivery point within a medium, wherein said fiber optic comprises a proximal end and a distal end, wherein said medium is selected from a group consisting of a portion of a human body and a portion of an animal body;
means for delivering a drug to said drug delivery point; and
means for coupling laser light into said proximal end, wherein said laser light has (i) a pulse frequency within the range of 100 Hz to 1 MHz, (ii) a wavelength within the range of 200 nm to 5000 nm, (iii) a pulse duration within the range of 1 fs to 1 ms and (iv) an energy density within the range of 0.01 $J/cm^2$ to 25 $J/cm^2$, wherein said laser light emerges from said distal end and generates an acoustic radiation field in said medium, wherein said acoustic radiation field is generated through one or more mechanisms selected from a group consisting of thermoelastic expansion within said medium and superheated vapor expansion within said medium, wherein said acoustic radiation field acts as a drug delivery enhancer.

52. An apparatus for enhancing drug delivery, comprising:
a fiber optic for insertion to a drug delivery site within a medium, wherein said fiber optic comprises a proximal end and a distal end, wherein said medium is selected from a group consisting of a portion of a human body and a portion of an animal body; and
means for delivering a drug to said drug delivery site; and
means for coupling laser light into said proximal end of said fiber optic for generating an acoustic radiation field within said medium near said drug delivery site, wherein said acoustic radiation field enhances the absorption of said drug.

53. The apparatus of claim 52, wherein said laser light has (i) a pulse frequency within the range of 100 Hz to 1 MHz, (ii) a wavelength within the range of 200 nm to 5000 nm, (iii) a pulse duration within the range of 1 fs to 1 ms and (iii) an energy density within the range of 0.01 $J/cm^2$ to 25 $J/cm^2$.

54. The apparatus of claim 52, wherein said drugs are selected from a group consisting of chemotherapeutic drugs, antibiotics, photodynamic drugs, and gene therapies.

55. The apparatus of claim 54, wherein said chemotherapeutic drugs are selected from a group consisting of Taxol, 5-Aminoaleuvenic acid and anthracyclines.

56. The apparatus of claim 54, wherein said photodynamic drugs are selected from a group consisting of psoralans and porphyrin derivatives.

57. The apparatus of claim 54, wherein said gene therapies are selected from up consisting of RNA therapies and DNA therapies.

58. The apparatus of claim 52, wherein said means for delivering a drug to said drug delivery site includes means for administering therapeutic compounds locally to said drug delivery site by delivering a drug through a delivery mechanism selected from a group consisting of a needle, a cannula and a vascular catheter.

59. The apparatus of claim 52, wherein said means for delivering a drug to said drug delivery site includes means for administering therapeutic compounds locally to said drug delivery site by utilizing mechanical barriers to limit diffusion of said compounds.

60. The apparatus of claim 59, wherein said mechanical barriers comprise a balloon catheter to dam said drug within a blood vessel.

61. The apparatus of claim 52, wherein said means for generating an acoustic radiation field comprise means for generating pressure within said medium, wherein said pressure is within a range of 0.1 bar to 100 bar.

62. The apparatus of claim 52, further comprising a catheter, wherein said fiber optic is located within said catheter.

63. The apparatus of claim 62, further comprising a working channel within said catheter, wherein said working channel may deliver to said drug delivery site at least one deliverable selected from a group consisting of a drug and an echo contrast agent.

64. The apparatus of claim 53, wherein said means for generating an acoustic radiation field comprise a laser system, wherein said fiber optic is coupled to said laser system.

65. The apparatus of claim 53, further comprising at least one medium selected from a group consisting of native fluids, an exogenous absorber and a solid absorber, wherein said laser light that emerges from said distal end of said fiber optic is absorbed by said at least one medium.

66. The apparatus of claim 65, wherein said native fluids comprise blood.

67. The apparatus of claim 65, wherein said exogenous absorber comprises a bio-compatible solution, such as saline solution, containing an absorbing dye.

68. The apparatus of claim 65, wherein said solid absorber is selected from a group consisting of plastic and metal.

69. The apparatus of claim 52, wherein said means for generating an acoustic radiation field comprise means for delivering pulses of electromagnetic energy from a laser into an absorber.

70. The apparatus of claim 50, wherein said means for generating an acoustic radiation field include means selected from a group consisting of means for plasma formation, means for material ablation, means for producing thermoelastic expansion and means for producing thermodynamic vaporization.

71. The apparatus of claim 53, wherein said means for generating an acoustic radiation field comprise a transducer affixed to said distal end of said fiber optic.

72. The apparatus of claim 71, wherein said transducer comprises material selected to match the acoustic impedance of said ambient medium for optimal transmission of acoustic energy.

73. The apparatus of claim 71, wherein said transducer comprises material selected to produce large impedance mismatches to reflect greater amounts of energy.

74. The apparatus of claim 53, further comprising a plurality of fiber optics, wherein said acoustic radiation field is produced by delivering said laser light through said plurality of fiber optics, wherein each fiber optic of said plurality of fiber optics comprises a distal end, wherein a transducer is affixed to each distal end.

75. The apparatus of claim 71, further comprising means for cooling said transducer.

76. The apparatus of claim 75, wherein said means for cooling said transducer comprise a convective cooling system, wherein waste heat produced at said distal end is mitigated by said convective cooling system, wherein a coolant removes heat from said transducer.

77. The apparatus of claim 52, further comprising an absorbing fluid filled optically-powered mechanical transducer attached to said distal end of said fiber optic.

78. The apparatus of claim 77, wherein said absorbing fluid filled optically-powered mechanical transducer is a cylinder-shaped diaphragm which expands and contracts with the formation and collapse of bubbles within said transducer.

79. The apparatus of claim 77, wherein said absorbing fluid filled optically-powered mechanical transducer comprises a bellows.

80. The apparatus of claim 53, further comprising an optically-powered mechanical transducer which comprises pores, wherein said drug is driven out of said transducer with the increased pressure caused by bubbles produced by said laser light.

81. The apparatus of claim 52, further comprising means for monitoring and controlling the magnitude of said acoustic radiation field with a feedback system.

82. The apparatus of claim 81, wherein said feedback system comprises piezoelectric materials in which an electrical signal is generated proportional to said acoustic radiation field.

83. The apparatus of claim 52, further comprising a thin film mounted at the end of said fiber optic, wherein the reflections of two surfaces of said thin film are monitored to determine the amplitude of said acoustic radiation field.

84. The apparatus of claim 71, further comprising a thin film mounted at the end of said transducer, wherein the reflections of two surfaces of said thin film are monitored to determine the amplitude of said acoustic radiation field.

85. The apparatus of claim 52, further comprising an echo contrast agent for delivery near said drug delivery site, wherein said echo contrast agent further enhances the absorption of said drug.

86. The apparatus of claim 85, wherein said echo contrast agent is selected from a group consisting of albumin-stabilized microbubbles, stabilized sulfur hexafluoride and galactose/palmitic acid.

87. The apparatus of claim 85, wherein said echo contrast agent comprises gas bubbles having a diameter within the range of 0.1–100 $\mu$m.

* * * * *